United States Patent [19]

Negishi et al.

[11] Patent Number: 5,480,787
[45] Date of Patent: Jan. 2, 1996

[54] TRANSESTERIFICATION METHOD USING LIPASE POWDER WITH A PARTICLE DIAMETER OF 20–50 MICRONS

[75] Inventors: Satoshi Negishi, Sagamihara; Seiichi Shirasawa, Ebina; Junko Suzuki, Yokohama; Tateo Murui, Tokyo, all of Japan

[73] Assignee: The Nisshin Oil Mills, Ltd., Tokyo, Japan

[21] Appl. No.: 296,921

[22] Filed: Aug. 31, 1994

[30] Foreign Application Priority Data

Sep. 17, 1993 [JP] Japan .................................. 5-231629

[51] Int. Cl.$^6$ .............................. C12P 7/64; C12P 7/62; C12N 9/20
[52] U.S. Cl. ........................... 435/134; 435/135; 435/198
[58] Field of Search ..................................... 435/134, 135, 435/198

[56] References Cited

U.S. PATENT DOCUMENTS

| | | | |
|---|---|---|---|
| 5,190,968 | 3/1993 | Kokusho et al. | 435/134 |
| 5,316,927 | 5/1994 | Zaks et al. | 435/134 |

FOREIGN PATENT DOCUMENTS

| | | |
|---|---|---|
| 58-36953 | 8/1983 | Japan . |
| 60-98984 | 6/1985 | Japan . |
| 61-202688 | 9/1986 | Japan . |
| 1-262795 | 10/1989 | Japan . |
| 2-138986 | 5/1990 | Japan . |
| 3-61485 | 3/1991 | Japan . |

OTHER PUBLICATIONS

Terrades F. et al, J. Am. Chem. Soc. 115:390–396 (1993).
Klibanov A. M., TIBS 14:141–144 (1989).

Primary Examiner—Marian C. Knode
Assistant Examiner—S. Saucier
Attorney, Agent, or Firm—Oblon, Spivak, McClelland, Maier & Neustadt

[57] ABSTRACT

The transesterification method is conducted with a powdery lipase wherein the powdery lipase is dispersed in ester-containing starting materials in the presence or absence of an inert organic solvent, and the diameter of at least 90% of the dispersed lipase particles is kept in the range of 1 to 100 μm in the course of the trans-esterification reaction. A reactivity higher than that realized by the conventional transesterification method with a powdery lipase is obtained and the lipase can be easily recovered and reused, without causing a loss of the lipase activity, lowering of the conversion due to the residence of the substrate on the immobilizing carrier and side reactions caused by water introduced into the reaction system by the immobilizing carrier.

13 Claims, 1 Drawing Sheet

EFFECT OF ULTRASONIC TREATMENT

TRANSESTERIFICATION METHOD USING LIPASE POWDER WITH A PARTICLE DIAMETER OF 20– 50 MICRONS

BACKGROUND OF THE INVENTION

The present invention relates to a transesterification method with a powdery lipase.

The transesterification reaction is an important means for the reforming of animal and vegetable oils and fats and also for the production of various fatty acid esters, saccharide esters and steroids. When a lipase which is an enzyme for hydrolyzing oils and fats is used as the catalyst for the transesterification reaction, the following merits are obtained: this reaction can be conducted under mild conditions of room temperature to about 70° C.; the side reactions can be controlled and the energy cost can be lowered more easily than in ordinary chemical reactions; and a high safety is attained, since the lipase used as the catalyst is a natural product. Another merit is that the intended product can be efficiently produced, based on the substrate specificity and site specificity.

However, when the powdery lipase is used as it is for the transesterification reaction, its activity cannot be sufficiently exhibited. Moreover, it is difficult to homogeneously disperse the essentially water-soluble lipase in the oily starting materials and, in addition, the recovery thereof is also difficult. Therefore, the lipase is usually immobilized on a carrier such as an anion-exchange resin [Japanese Patent Unexamined Published Application (hereinafter referred to as "J.P. KOKAI") No. Sho 60-98984), phenol adsorbent resin (J.P. KOKAI No. Sho 61-202688), hydrophobic carrier (J.P. KOKAI No. Hei 2-138986), cation-exchange resin (J.P. KOKAI No. Hei 3-61485) or chelate resin (J.P. KOKAI No. Hei 1-262795) in order to use it for the transesterification reactions of the oils and fats.

Although the lipase to be used for the transesterification reaction was immobilized in the prior art, the immobilization causes a loss of the essential activity of the lipase and, in addition, when a porous carrier is used, the pores are clogged with the starting materials and the product to lower the transesterification efficiency. Further, in the transesterification reaction with the conventional immobilized lipase, water contained in the carrier is introduced into the reaction system and, therefore, it is difficult to avoid side reactions such as the formation of a diglyceride or monoglyceride in the course of the transesterification reaction of the oils and fats.

It has been scarcely known in the field of the transesterification reaction with the ordinary lipase that a lipase is usable at a reaction temperature of as high as around 100° C. whether the lipase is immobilized or not. The reasons therefor are supposedly that no lipase resistant to such a high temperature has been found yet and that such a heat-resistant, immobilized lipase was not developed in the conventional immobilization technique.

SUMMARY OF THE INVENTION

A primary object of the present invention is to provide a transesterification method wherein a reactivity higher than that realized by the conventional transesterification method with a powdery lipase is obtained and the lipase can be easily recovered and reused, without causing a loss of the lipase activity, lowering of the conversion due to the residence of the substrate on the immobilizing carrier and side reactions caused by water introduced into the reaction system by the immobilizing carrier.

This and other objects of the present invention will be apparent from the following description and Examples.

The present invention has been completed on the basis of a finding that the above-described problems can be solved by dispersing a powdery lipase in the starting materials to be subjected to the transesterification reaction and controlling the particle size of the powdery lipase so that the diameter of at least 90% of the particles is in the range of 1 to 100 μm.

Namely, the present invention provides a transesterification method with a powdery lipase wherein the powdery lipase is dispersed in ester-containing starting materials in the presence or absence of an inert organic solvent, and the diameter of at least 90% of the dispersed lipase particles is kept in the range of 1 to 100 μmin the course of the trans-esterification reaction.

PREFERRED EMBODIMENT OF THE INVENTION

Figure 1:
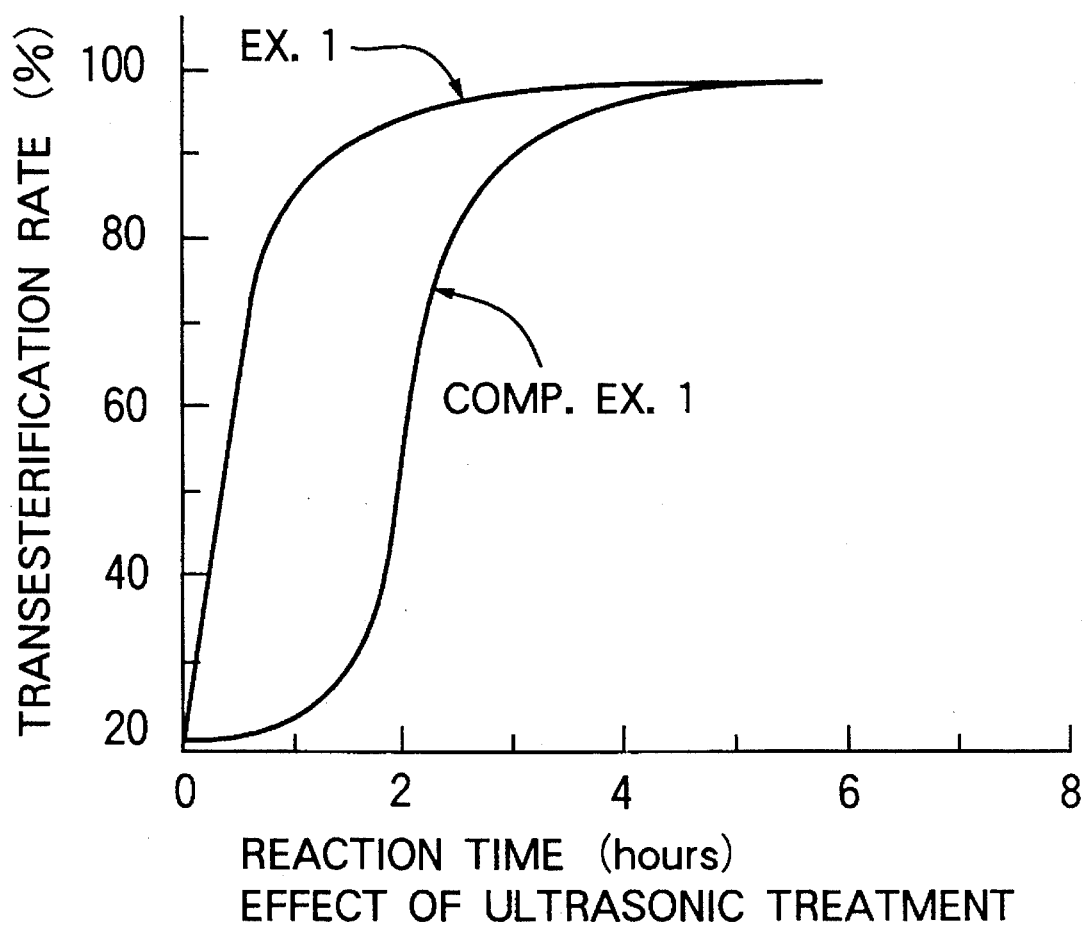
FIG. 1 shows the changes of the degree of transesterification with time observed when the starting materials were subjected to the ultrasonic treatment (Example 1) and also when they were not subjected thereto (Comparative Example 1).

The esters usable herein include those derived from a carboxylic acid and an alcohol. The carboxylic acids used for forming the esters are preferably saturated or unsaturated, linear or branched aliphatic monobasic acids, so called fatty acids, having 2 to 40 carbon atoms, and aliphatic dibasic acids and tribasic acids having 2 to 30 carbon atoms. Examples of the aliphatic monobasic acids include acetic acid, butyric acid, caprylic acid, isooctylic acid, isononanoic acid, capric acid, lauric acid, palmitic acid, palmitooleic acid, heptadecanoic acid, stearic acid, isostearic acid, oleic acid, elaidic acid, 10-hydroxystearic acid, 12-hydroxystearic acid, ricinoleic acid, linoleic acid, linolenic acid, erucic acid, behenic acid, arachidonic acid, eicosapentaenoic acid, docosahexaenoic acid, cerotic acid, montanic acid, nonacosanoic acid and melissic acid. Examples of the aliphatic dibasic acids include succinic acid, malic acid, fumaric acid, maleic acid, tartaric acid, glutaric acid, azelaic acid, sebacic acid, 1,12-dodecadicarboxylic acid and 1,24-tetracosadicarboxylic acid. Examples of the aliphatic tribasic acids include citric acid.

The alcohols are preferably saturated or unsaturated, linear or branched aliphatic monohydric alcohols and dihydric to hexahydric alcohols having 1 to 50 carbon atoms. Examples of the alcohols include monohydric alcohols such as methanol, ethanol, isopropyl alcohol, hexanol, isooctanol, isononanol, lauryl alcohol, cetanol, stearyl alcohol, isostearyl alcohol, oleyl alcohol, behenyl alcohol, octacosanol, UNILIN® alcohol 425 (average molecular weight: 510, a product of Petrolite Corp., U.S.A.), UNILIN® alcohol 550 (average molecular weight: 660) and UNILIN® alcohol 700 (average molecular weight: 850); dihydric alcohols such as ethylene glycol, diethylene glycol, propylene glycol, dipropylene glycol, butylene glycol, neopentyl glycol, 1,8-octanediol and 1,10-decanediol; and trihydric and higher hydric alcohols such as glycerol, diglycerol, triglycerol, polyglycerols, pentaerythritol, trimethylolethane and trimethylolpropane. The upper limit of the number of the carbon atoms in the above-described carboxylic acids and alcohols suggests that the carboxyic acids and alcohols are those available on an industrial scale on the market. Of course, the carboxylic acids and alcohols having more carbon atoms are usable so far as they are easily available.

The esters derived from the carboxylic acid and alcohol can be extracted from natural products such as animals, vegetables, marine animals, microorganisms and minerals, or they can be synthesized by esterification by an ordinary method. Preferred examples of the esters are oils, fats and waxes in the present invention.

In the present invention, the powdery lipase is added to the above-described ester used as the starting material to conduct the transesterification reaction. The esters are usable either singly or in the form of a mixture of them, If necessary, the ester is usable in combination with one or more of the above-described carboxylic acids or one of more of the above-described alcohols. It is indispensable, however, that the starting material in which the powdery lipase is to be dispersed is the ester. When the powdery lipase is directly added to the carboxylic acid or alcohol, the activity of the lipase is lowered to prolong the transesterification reaction time unfavorably. It is preferred, therefore, that when the carboxylic acid or alcohol and the ester are used as the starting materials, the powdery lipase is previously dispersed in at least the ester and then the carboxylic acid or alcohol is added thereto in the present invention. Although the powdery lipase can be directly added to the starting material, it is convenient to use an organic solvent inert to the starting-material (reaction substrate) and lipase, such as a hydrocarbon, e.g. hexane or heptane. The inert organic solvent is used preferably in an amount of 10 to 90 parts by weight for 100 parts by weight of the starting material. The reaction can be conducted under appropriate heating so far as the activity of the lipase is not impaired.

The present invention is characterized in that the diameter of at least 90% of the particles of the lipase dispersed as described above is controlled in the range of 1 to 100 μm, preferably 20 to 50 μm, in the course of the transesterification reaction. In particular, when the powdery lipase is added to the ester, small masses having various sizes of several hundred μm or above are formed to form a heterogeneous dispersion. This dispersion is homogenized so that the particle size will be in the above-specified range. The homogenization is conducted by an ultrasonic treatment of the inert organic solvent and/or ester containing the powdery lipase dispersed therein, or a method wherein the dispersion is suitably stirred, if necessary, and then it is subjected to the microfiltration or centrifugal precipitation. The dispersion in which the diameter of at least 90% of the lipase particles dispersed therein is in the range of 1 to 100 μm can be obtained by one or a combination of the above-described methods and, if necessary, by determining the particle diameter and distribution with a granulometer. The ultrasonic treatment is preferred, since it is simple and easy. The ultrasonic treatment is conducted under the conditions of 20 to 150 kHz and 1 to 30 minutes. When the amount of the dispersed lipase particles having a diameter of 1 to 100 μm is below 90%, the reactivity is reduced (in case the particle diameter is larger) or the recovery of the lipase particles from the reaction liquid is difficult to make the reuse thereof impossible (in case the particle diameter is smaller).

Thus, in the present invention, the particle size of the powdery lipase before use is unimportant and any powdery lipase which can be finely divided by the above-described method after the addition to the ester is usable. Usually, powdery lipase having an average particle diameter of 10 to 100 μm is preferred.

After the diameter of the dispersed lipase particles is thus controlled at a desired size, the dispersion is mixed with the ester in case the dispersion medium is the inert organic solvent and then mixed with the carboxylic acid or alcohol to conduct the transesterification reaction. In case the dispersion medium is the ester, the dispersion is subjected to the reaction directly or after suitably adding the carboxylic acid or alcohol. The particle diameter of the lipase in the course or after completion of the transesterification reaction is controlled by determining the size of the particles in the reaction liquid and, if necessary, treating the reaction liquid by one or a combination of the above-described methods.

The powdery lipase usable in the present invention may be obtained from any of animals, vegetables and microorganisms. Examples of them include lipase obtained from the pancreas of swine, lipase obtained from soybeans, rice bran, castor beans, etc., and lipase produced by *Aspergillus niger, Candida cylindracea, Rhizopus delemar, Rhizopus javanicus*, Alcaligenes sp., *Alcaligenes faecalis, Mucor miehei* and *Pseudomonas fluorescens*. Although the lipase can be produced by extraction from the above-described tissues or culture liquids followed by purification, it is convenient to use a commercially available lipase.

Among the lipases described above, one produced by Alcaligenes sp. is preferred. In particular, preferred is Lipase QL (a product of Meito Sangyo Co., Ltd.) produced by a lipase-producing microorganism, Meito PL-266, and deposited at the Fermentation Research Institute of the Agency of Industrial Science and Technology as FERM P-3187 and FERM BP-2985 as described in Japanese Patent Publication for Opposition Purpose (hereinafter referred to as "J.P. KOKOKU") No. Sho 58-36953. This lipase is a bile activation lipase having the site specificity to the 1-position and 3-position of a glyceride and an optimum pH on the alkaline side. The enzymatic properties of this lipase are described in J.P. KOKOKU No. Sho 58-36953. Another lipase, lipase PL (a product of Meito Sangyo Co., Ltd.) obtained from Alcaligenes sp. is also usable. When such a lipase is used, the transesterification reaction can be conducted at a temperature of as high as 81° to 130° C. In the course of the reaction, the reaction system can be made substantially free from water to inhibit the decomposition reactions. Another advantage is that a starting material having a high melting point, such as a wax, can be used in the solvent-free reaction system. Concretely, the lipase is added to the starting substrate to be transesterified without addition of water, and the mixture is heated to 81° to 130° C., preferably 91° to 120° C., more preferably 91° to 110° C., and most preferably 95° to 100° C. in the absence of any solvent, the diameter of the dispersed particles is controlled at the predetermined size by the above-described method, and the reaction is conducted for a predetermined period of time such as 10 minutes to 50 hours. After the completion of the reaction, the reaction product is recovered and purified by an ordinary method to obtain the transesterification reaction product.

When the transesterification reaction is conducted at a temperature of not as high as that described above, the reaction is conducted at a temperature around an optimum temperature for the lipase to be used, preferably under anhydrous condition for 10 minutes to 50 hours. After the completion of the reaction, the reaction product is recovered and purified by an ordinary method to obtain the transesterification reaction product. In the present invention, the dispersed lipase particles can be recovered from the reaction liquid by the microfiltration, centrifugation, washing with an inert organic solvent or the like, and used again for the transesterification reaction after controlling the particle size, if necessary, by the above-described method.

According to the present invention, a higher reactivity than that obtained by the ordinary transesterification method with the powdery lipase can be obtained, and the lipase can be easily recovered and reused. Further, the transesterification reaction of a high-melting fat such as a wax can be easily and efficiently conducted in the absence of any solvent. In addition, the preparation of the immobilized lipase is unnecessary and, therefore, the lowering of the reactivity (namely, prolongation of the reaction time) and side reactions caused by water can be prevented unlike the transesterification method wherein the immobilized lipase is used.

The following Examples will further illustrate the present invention.

EXAMPLE 1

50 g of a medium chain length fatty acid triglyceride (trade name: ODO; a product of The Nisshin Oil Mills, Ltd.) having a caprylic acid/capric acid ratio of 75/25 was fed into a 200 ml flask provided with a stirrer. 0.1 g of a powdery lipase (trade name: Lipase QL, average particle diameter: 30 μm; a product of Meito Sangyo Co., Ltd.) produced by Alcaligenes sp. was added thereto. The resultant mixture was treated by 10-second cycle irradiation with ultrasonic waves by using an ultrasonic generator (SUS-103; a product of Shimadzu Corporation) under the conditions of room temperature, 28, 45 and 100 kHz for 1 minute. After the completion of the treatment, the lipase particle distribution in the dispersion was determined with a particle size distribution meter (multisizer, a product of Coulter Electronics) to find that 98% of the particles had a diameter of 20 to 50 μm. Then 50 g of triolein was added to the dispersion, and the resultant mixture was stirred at a rotational speed of 350 rpm at 75° C. to conduct the transesterification reaction. The degree of transesterification was determined with time intervals to check the progress of the reaction. The degree of transesterification was determined by analyzing the glyceride composition by a gas chromatography and calculating the proportion of the transesterification reaction products in the sample.

The change of the degree of transesterification with time in Example 1 is shown in FIG. 1. It is apparent from FIG. 1 that by the process of the present invention, a high activity was obtained soon after initiation of the reaction, and the reaction was completed in about 3 hours.

Comparative Example 1

The transesterification reaction was conducted in the same manner as that of Example 1 except that the ultrasonic treatment was not conducted prior to the reaction and that the stirring rate was changed to 200 rpm. 90% of the lipase particles had a diameter of 500 to 800 μm. The results are shown in FIG. 1, which indicates that the transesterification reaction did not proceed for about 2 hours after the start and that about 5 hours were necessitated for the completion of the reaction.

EXAMPLE 2

0.5 g of a powdery lipase (trade name: Lipase PL; a product of Meoto Sangyo Co., Ltd.) produced by Alcaligenes sp. was added to a mixture of 50 g of palm oil and 50 g of rape oil. After the same ultrasonic treatment as that of Example 1 except that the conditions were 50 kHz and 5 min, a dispersion in which 92% of the lipase particles had a diameter of 20 to 50 μm was obtained. Then the transesterification reaction was conducted under slow stirring at 60° C. for 24 hours. The degree of transesterification was 97%. Then the lipase particles were recovered from the reaction liquid with a microfilter (Toyo Filter Paper No. 5C; pore diameter: 1 μm), and directly added to a fresh starting mixture of 50 g of palm oil and 50 g of rape oil to conduct the transesterification reaction in the same manner as that described above. After thus repeating the transesterification reaction five times in total, the recovered lipase particles were degreased by washing with hexane and then used again for the transesterification reaction. Since the lipase activity was recovered to the same level as that in the first and the second reaction steps, the lipase was further used repeatedly for the transesterification reaction. Thus, the batchwise reaction could be repeated about 40 times while the initial activity was kept, and about 7,000 parts by weight, per part by weight of the powdery lipase used, of the oils could be transesterified.

EXAMPLE 3

0.1 g of a powdery lipase (trade name: Lipase OF; a product of Meito Sangyo Co., Ltd.) produced by Candida cylindracea was suspended in 30 g of safflower oil. The resultant suspension was filtered through a nylon filter cloth (pore diameter: 100 μm) and the same microfilter (pore diameter: 1 μm) as that used in Example 2 to obtain a dispersion wherein the lipase particles had a diameter of 1 to 100 μm. 30 g of palm oil was added to the dispersion, and the resultant mixture was stirred at a speed of 100 rpm with a magnetic stirrer at 60° C. to conduct the transesterification reaction. The transesterification reaction rapidly proceeded to complete the reaction 4 hours after the start of the reaction.

Comparative Example 2

The transesterification reaction was conducted in the same manner as that of Example 3 except that the powdery lipase was directly added to the starting materials and that the pretreatment was not conducted. 10% of the lipase particles in the reaction liquid had a diameter of 10 to 90 μm, and the particle diameter of the balance exceeded 100 μm. As a result, when the stirring speed was 100 rpm, the lipase particles were too large to conduct the transesterification reaction.

EXAMPLE 4

The transesterification reaction was conducted by using 50 g of ethyl esters of decomposed fatty acids of montan wax (trade name: S wax, a product of Hoechst), 50 g of ODO (the same as that used in Example 1) and 1 g of lipase QL, at a stirring speed of 300 rpm with a magnetic stirrer. The reaction was conducted at a temperature of 95° C. which was above the melting point of the montan wax for 7 hours. The powdery lipase was dispersed in ODO and treated in the same manner as that of Example 1 prior to the reaction. 96% of the lipase particles had a diameter of 20 to 40 μm.

From the results of the gas chromatographic analysis of the reaction products, the introduction of the montan wax fatty acids into ODO (triglyceride) was confirmed. From this fact, it was found that the wax which is a high-melting fat could be transesterified with the lipase at a temperature of as high as 95° C. without using any solvent.

EXAMPLE 5

The transesterification reaction was conducted by using 20 g of a dibasic acid having 14 carbon atoms, 80 g of tributyrin (glycerol tributyrate) (trade name: Tributyrin; a product of Wako Pure Chemical Industries, Ltd.) and 1 g of lipase QL as used in Example 1, at a stirring speed of 300 rpm with a magnetic stirrer. The reaction was conducted at a temperature of 120° C. in order to dissolve the long-chain dibasic acid. The reaction time was 6.5 hours. The powdery lipase was dispersed in tributyrin and treated in the same manner as that of Example 1 prior to the reaction. 90% of the lipase particles had a diameter of 10 to 90 μm.

From the results of the gas chromatographic analysis of the reaction products, the introduction of the long-chain dibasic acid into tributyrin was confirmed. From this fact, it was found that the long-chain dibasic acid which is a high-melting fat could be transesterified with the lipase at a temperature of as high as 120° C. without using any solvent.

Comparative Example 3

Lipase OF as used in Example 3 was dissolved in water to obtain 10% aqueous solution. 50 g of Celite was added to 100 ml of the solution, and the resultant mixture was freeze-dried to obtain an immobilized lipase having a water content of 0.1% and particle diameter of 0.1 to 1.4 mm. 2 g of the immobilized lipase was added to a mixture of 30 g of safflower oil and 30 g of palm oil to conduct the transesterification reaction in the same manner as that of Example 3. The time necessitated for the completion of the reaction was 15 hours. The reaction product was analyzed by GLC to find that 7.5% of the diglyceride which was not detected in other Examples was contained in the product.

What is claimed is:

1. A method of transesterification with a powdered lipase, comprising:

dispersing a powdered lipase in an ester starting material in the presence or absence of an inert organic solvent; and conducting said transesterification in a reaction liquid under conditions which maintain the diameter of at least 90% of the dispersed lipase particles within the range of 20 to 50 μm.

2. The method of transesterification of claim 1, wherein the powdered lipase is produced by a microorganism of the genus Alcaligenes.

3. The method of transesterification of claim 1, wherein the transesterification reaction is conducted at 81° to 130° C.

4. The method of transesterification of claim 1, wherein the ester starting materials is obtained by the reaction of a fatty acid having 2 to 40 carbon atoms with an alcohol having 1 to 50 carbon atoms.

5. The method of transesterification of claim 1, wherein the powdered lipase is dispersed in an ester starting material in the absence of an inert organic solvent.

6. The method of transesterification of claim 1, wherein the diameter of at least 90% of the dispersed lipase particles is kept within the range of 20 to 50 μm by a method selected from the group consisting of (i) subjecting the inert organic solvent containing the powdered lipase dispersed therein to an ultrasonic treatment, (ii) subjecting the starting material containing the powdered lipase dispersed therein to an ultrasonic treatment, and (iii) subjecting the inert organic solvent and starting materials containing the powdered lipase dispersed therein to an ultrasonic treatment, and subsequently effecting separation of the lipase from the transesterification reaction liquid by microfiltering the transesterification reaction liquid and washing the filtered lipase with an inert organic solvent.

7. The method of transesterification of claim 1, wherein the transesterification reaction is conducted for 10 minutes to 50 hours.

8. The method of transesterification of claim 1, wherein the powdered lipase is dispersed in the absence of an inert organic solvent.

9. The method of transesterification of claim 1, wherein the powdered lipase is dispersed in the presence of an inert organic solvent.

10. A method of transesterification with a powdered lipase produced by a microorganism of the genus Alcaligenes, which comprises the steps of:

dispersing the powdered lipase in ester starting material in the absence of an inert organic solvent;

maintaining the diameter of at least 90% of the dispersed lipase particles within the range of 20 to 50 μm during the course of transesterification; and conducting the transesterification in a reaction liquid at 81° to 130° C. for 10 minutes to 50 hours.

11. The method of transesterification of claim 10, wherein the transesterification reaction is conducted at 91° to 120° C.

12. The method of transesterification of claim 10, wherein the ester starting material is obtained by the reaction of fatty acid having 2 to 40 carbon atoms with an alcohol having 1 to 50 carbon atoms.

13. The method of transesterification of claim 10, wherein the diameter of at least 90% of the dispersed lipase particles is kept within the range of 20 to 50 μm by subjecting the starting material containing the powdered lipase dispersed therein to an ultrasonic treatment, and subsequently effecting separation of the lipase from the transesterification reaction liquid by microfiltering the reaction liquid and washing the filtered lipase with an inert organic solvent.

* * * * *